US007371351B2

(12) United States Patent
Goswami (10) Patent No.: US 7,371,351 B2
(45) Date of Patent: May 13, 2008

(54) PHOTOELECTROCHEMICAL AIR DISINFECTION (75) Inventor: Dharendra Yogi Goswami, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 198 days.

(21) Appl. No.: 11/411,312

(22) Filed: Apr. 26, 2006

(65) Prior Publication Data

US 2006/0188387 A1    Aug. 24, 2006

Related U.S. Application Data (63) Continuation of application No. 10/462,424, filed on Jun. 16, 2003, now Pat. No. 7,063,820.

(51) Int. Cl.
*B01J 19/08* (2006.01)

(52) U.S. Cl. .................. 422/120; 422/122; 422/186.3

(58) Field of Classification Search ............... 422/120, 422/122, 186.3; 204/157.3; 96/16, 98
See application file for complete search history.

(56) References Cited

U.S. PATENT DOCUMENTS

| 5,137,607 | A | 8/1992 | Anderson et al. |
| 5,863,491 | A | 1/1999 | Wang |
| 5,993,702 | A | 11/1999 | Davis |
| 5,993,738 | A | 11/1999 | Goswami |
| 6,315,963 | B1 | 11/2001 | Speer |
| 6,501,893 | B1 | 12/2002 | Imiura |
| 6,752,884 | B2 | 6/2004 | Min |
| 2003/0098101 | A1 | 5/2003 | Min |
| 2004/0022700 | A1 | 2/2004 | Kim et al. |

FOREIGN PATENT DOCUMENTS

| JP | 200093808 | 4/2000 |
| JP | 2002030552 | 1/2002 |
| JP | 2002085978 | 3/2002 |

*Primary Examiner*—Gladys J P Corcoran
*Assistant Examiner*—Sean E Conley
(74) *Attorney, Agent, or Firm*—Lott & Friedland, P.A.

(57) ABSTRACT

A system for disinfecting a fluid containing microorganisms or chemical contaminants includes a plurality of photocatalyst surfaces secured to a solid surface upon which a fluid to be disinfected contacts. A structure for removing a portion of the photogenerated electrons is in electrical contact with the photocatalyst layer, wherein an electron-hole recombination rate involving the photogenerated electrons and holes is reduced, thus increasing the removal rate of microorganisms or chemical contaminants from the fluid. The system can include a source of photons having a wavelength corresponding to a band gap energy of the photocatalyst to illuminate the photocatalyst layer. The invention can be used in air supply registers of a heating, ventilating and air conditioning system, or in air ducts, or used to disinfect wall coverings, floor coverings, envelopes, packages, and clothing articles.

16 Claims, 5 Drawing Sheets

PHOTOELECTROCHEMICAL AIR DISINFECTION

CROSS-REFERENCE TO RELATED APPLICATIONS

This application is a continuation of U.S. patent application Ser. No. 10/462,424 entitled "PHOTOELECTROCHEMICAL AIR DISINFECTION" filed on Jun. 16, 2003, the entirety of which is incorporated herein by reference.

STATEMENT REGARDING FEDERALLY SPONSORED RESEARCH OR DEVELOPMENT

Not applicable.

FIELD OF THE INVENTION

The invention relates to systems and methods for disinfecting fluids using photoelectrochemical processes enhanced by electron shunting.

BACKGROUND

Several microbiological particle control systems exist. Mechanical and electrostatic filters can be used to reduce indoor concentrations of respirable particles, such as in a forced air heating/cooling system of a building. Microbiological filters have been used for disinfection of air and other gases because of their low cost and ease of handling. These filters can be constructed to remove not only microorganisms, but also submicron particles as well. For efficient and economic operation of these filters, the aerosol content of the air to be filtered must be low, where the term "aerosols" generally refers to microorganisms, particles, and droplets of liquid dispersed in air. A disadvantage of such filters is that they do not permanently remove the contaminants, but just transfer them to the filter medium. Clogging of the filter medium can result which can cause high pressure drops. In addition, microorganisms trapped on the filter media continue to multiply making the filter media a breeding ground and thus hazardous.

Another method of microbiological particle removal is UV disinfection. UV disinfection has been widely used to destroy biological contaminants and toxic chemicals. Such UV treatment has worked well for disinfection, but the indoor environment may also be contaminated with low level toxic chemicals such as formaldehyde, styrene, and toluene. Ultraviolet energy alone has proven generally ineffective in degrading these chemicals. For instance, U.S. Pat. No. 5,045,288 to Raupp and Dibble, and U.S. Pat. Nos. 4,892,712; 4,966,759; and 5,032,241 to Robertson and Henderson disclose use of UV to treat fluids and gases that contain pollutants.

Another alternative that has gained increasing attention is photocatalytic oxidation (PCO), which involves the use of a photocatalyst such as $TiO_2$ for the destruction of hydrocarbons and microorganisms in fluids. Titanium dioxide ($TiO_2$) is a semiconductor photocatalyst with a room temperature band gap energy of about 3.2 eV. When this material is irradiated with photons having wavelengths less than about 385 nm (UV), the band gap energy is exceeded and electrons are generated through promotion from the valence band to the conduction band which results in the generation of holes (h+). The resulting highly reactive electron-hole pairs have lifetimes in the space-charge region of the photocatalyst that enables participation in chemical reactions, provided recombination events do not occur first. The most widely postulated chemical reactions are shown below:

$OH^- + h+ \rightarrow OH$ (hydroxyl radical)

$O_2 + e- \rightarrow O_2^-$ (super-oxide ion)

Hydroxyl radicals and super-oxide ions are highly reactive species that can readily oxidize volatile organic compounds (VOCs) adsorbed on catalyst surfaces. They can also kill and oxidize adsorbed bioaerosols. The process is a form of heterogeneous photocatalysis, or more specifically PCO.

Several attributes of PCO make it a strong candidate for indoor air quality applications. Pollutants, particularly VOCs, are preferentially adsorbed on photocatalytic surfaces and oxidized primarily to carbon dioxide ($CO_2$). Thus, rather than simply changing the phase and concentrating the contaminant, the absolute toxicity of the treated air stream is reduced, allowing the photocatalytic reactor to operate as a self-cleaning filter.

Photocatalytic reactors may be integrated into new and existing heating, ventilation, and air conditioning (HVAC) systems due to their modular design, room temperature operation, and generally negligible pressure drop. PCO reactors also feature low power consumption, potentially long service life, and low maintenance requirements. These attributes contribute to the potential of PCO technology to be an effective process for removing and destroying low level pollutants in indoor air, including bacteria, viruses and fungi.

For example, U.S. Pat. No. 5,933,702 to the same inventor as the present application discloses a method for disinfecting an air stream containing microorganisms. The method includes the steps of providing an air stream containing microorganisms having a relative humidity greater than about 40% and contacting the air stream with a photocatalyst having a predetermined band gap energy in the presence of a source of photons having a wavelength corresponding to the band gap energy of the photocatalyst. At least a portion of the microorganisms in the air stream are destroyed by photocatalytic oxidation. Improved devices embodying the method of the invention are disclosed, such as stand-alone devices and devices incorporated into the HVAC systems of buildings, including the air supply registers. Photocatalyst-coated filter media capable of trapping bioaerosols are also disclosed. U.S. Pat. No. 5,933,702 is hereby incorporated by reference into the current application in its entirety.

However, even the improved methods and devices disclosed in U.S. Pat. No. 5,933,702 have efficiencies which are limited by a generally slow photocatalytic oxidation process. The slow photocatalytic oxidation process results mainly because a large percentage of photo-generated electrons recombine with photo-generated holes before the holes have a chance to participate in a photocatalytic reaction.

SUMMARY OF THE INVENTION

A system for disinfecting a fluid containing microorganisms or chemical contaminants includes a plurality of photocatalyst surfaces secured to a solid surface upon which a fluid to be disinfected contacts. The system can be disposed in an air supply register of a heating, ventilating and air conditioning system or in an air duct. A structure for removing a portion of the photogenerated electrons is in electrical contact with the photocatalyst layer and provides an electrically conductive path for photo generated electrons to move away from photo generated holes. As a result, the electron-hole recombination rate involving the photogenerated electrons and holes is reduced, thus increasing the quantum efficiency of the photocatalytic oxidation process and the destruction rate of microorganisms or chemical contaminants present in the fluid.

The system can include a source of photons having a wavelength corresponding to a band gap energy of the photocatalyst to illuminate the photocatalyst layer. The photocatalyst layer can include a plurality of metal ions, such as Ag+. The fluid can be a liquid or an air stream.

The structure for removing a portion of the photogenerated electrons can comprise an electron conducting path such as a metallic grid in contact with the photocatalyst layer, the metallic grid including a plurality of metallic strips. Gaps between the strips allow photons to reach the photocatalyst. The plurality of metal strips can be connected to an external ground. Alternatively, a source of electrical bias connected to the metal grid, the bias increasing the rate of removal of the photogenerated electrons.

The structure for removing a portion of the photogenerated electrons can comprise at least one material generally toxic to microorganisms, such as silver.

A method for disinfecting fluids includes the steps of providing a photocatalyst layer comprising a plurality of photocatalyst particles, illuminating the photocatalyst layer with a source of photons having a wavelength corresponding to a band gap energy of the photocatalyst, wherein photogenerated electrons and holes are produced. A portion of the photogenerated electrons are removed, wherein a lower concentration of photogenerated electrons remain for electron-hole recombination reactions increasing removal efficiency of microorganisms or chemical contaminants from the fluid stream. The fluid stream is contacted with the photocatalyst layer, wherein at least a portion of the microorganisms or chemical contaminants in the fluid stream are photocatalytically oxidized.

A system for disinfecting air comprises a duct through which air is moved, a blower connected to the duct to move air through the duct, a photocatalyst layer including a plurality of photocatalyst particles having a predetermined band gap energy secured to a solid surface in the duct, structure for directing the photogenerated electrons away from photogenerated holes disposed in contact with the photocatalyst layer, and a source of photons for illuminating the photocatalyst with photons having a wavelength corresponding to the band gap energy of the photocatalyst. The solid surface can comprise at least one interior wall of the duct, the photocatalyst layer and the structure for directing being coated onto the wall.

A coating for disinfecting surfaces comprises a photocatalyst layer including a plurality of photocatalyst particles for photogenerating electrons and holes, the photocatalyst particles secured to a solid surface, and structure for removing a portion of the photogenerated electrons, wherein an electron-hole recombination rate involving the photogenerated electrons and holes is reduced increasing a removal rate of microorganisms or chemical contaminants from the surface. The solid surface can comprise wall coverings, floor coverings, envelopes, packages or clothing articles.

A method for disinfecting surfaces comprises the steps of providing a surface including a photocatalyst layer comprising a plurality of photocatalyst particles secured to the surface for photogenerating electrons and holes, contacting an electrically conducting structure to the photocatalyst layer, and illuminating the photocatalyst layer with UV light, wherein a portion of electrons generated by the photocatalyst particles are shunted by the electrically conducting structure. The providing step can comprise applying the photocatalyst layer to wall coverings, floor coverings, envelopes, packages, or clothing articles. The contacting and illuminating steps can be automated.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

A photocatalytic reactor-based system and related method for disinfecting fluids containing microorganisms or chemical contaminants increases the speed and efficacy of contaminant destruction significantly compared to previous systems by significantly reducing the rate of hole-electron recombination reactions. In contrast to previous advanced photocatalytic-based systems such as U.S. Pat. No. 5,933,702 which requires minimum relative humidity levels of 40% or more to achieve reasonable rates for the photocatalysis process, the present invention can operate efficiently at much lower relative humidity levels because of the reduced recombination. Effectively a larger number of active reactive sites per unit photocatalyst particle are provided by the invention. Accordingly, the invention can be used even when relative humidity is less than about 30%, while still providing substantially complete disinfection of air. Although, the invention is generally applied to air or other gases, the invention can be adapted for use in destroying contaminants present in liquid media, such as water.

Figure 1:
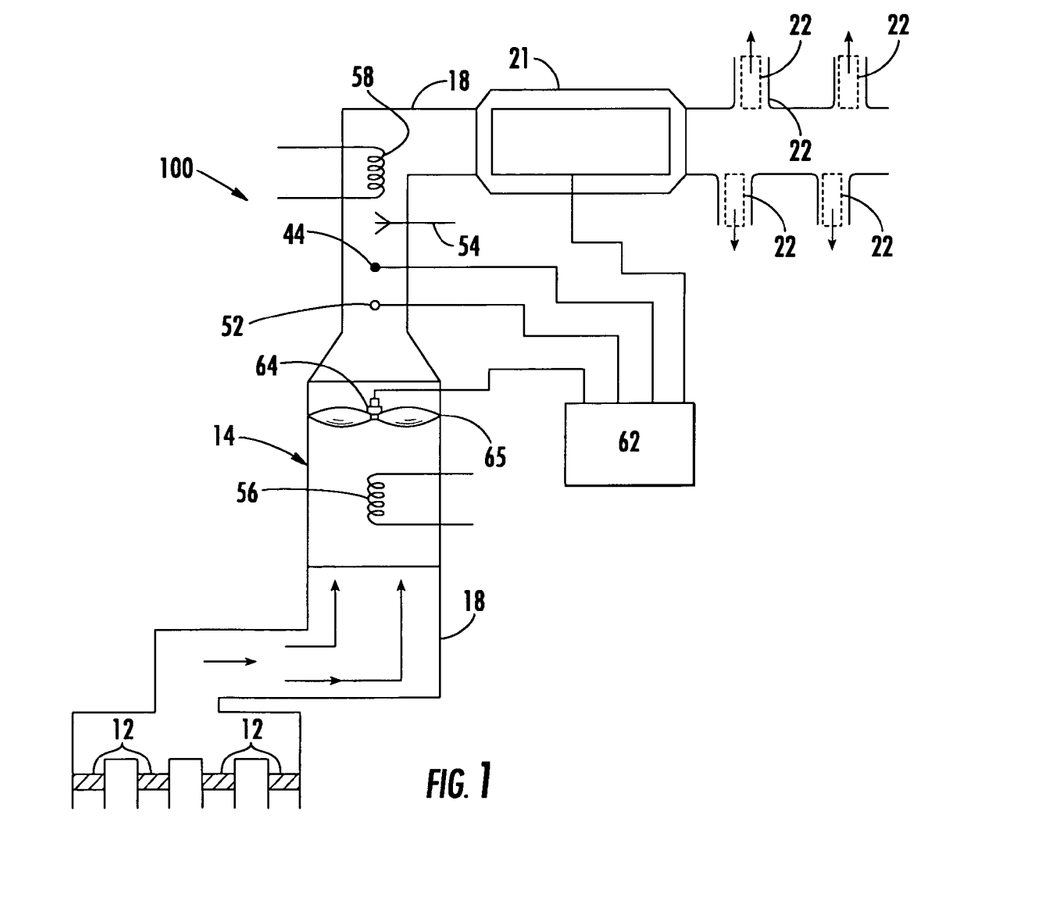
FIG. 1 is a diagrammatic-schematic of a typical heating/cooling duct system for a building with a reactor system having this invention incorporated therein, according to an embodiment of the invention.

FIG. 1 is a diagrammatic-schematic of a typical heating/cooling duct system 100 for a building with a reactor system having this invention incorporated therein, according to an embodiment of the invention. In most buildings, a blower/fan causes the air from the various zones of an air conditioned space to be drawn into a duct system via inlet openings and particle/aerosol filters 12. The air then can pass over the heating coil of the furnace or the heating/cooling coil of an air conditioner/heat pump of the air conditioning unit 14.

The fan 65 of the air handling unit 14 forces the air passing over coils 56 and 58 into a duct system 18. Detector 52 detects the humidity level in the air. Coils are used to condense water vapor, if the relative humidity in the air is above a predetermined level, such as 70%. Water spray or atomizer 54 adds moisture to the air stream if the humidity level measured by detector 52 is below a predetermined level, such as 30%.

In FIG. 1 there is a master reactor 21 along the duct 18. In many installations this will be sufficient. However, in the embodiment shown in FIG. 1, there is also shown a series of reactor units 22 disposed in branch lines of duct system 18. Reactor units 21 and 22 include a plurality of photocatalyst particles secured to a solid surface and at least one UV light source and structure for removing photogenerated electrons, exemplary embodiments being shown in FIGS. 2 and 3.

In FIG. 1 a conventional flow or speed detector 44, such as a Mamac Anubar flow detector can be located in the main duct system 18. Speed detectors are oftentimes placed within each reactor 22 and it is that type of reactor which is described with respect to the stand-alone units described hereinafter.

The faster the air speed, the less time air will be retained over the catalytic surfaces. As speed or volumetric displacement is lowered, retention time increases. It is usually desirable to maintain air movement throughout the building at all times. Here, the air speed can be adjusted for a maximum destruction of the deleterious matter by controlling the retention time over the photocatalytic surface.

This retention time will vary depending on the air flow rate, the size of the ducts, the area of the catalytic surfaces and other physical characteristics. The air speed or volume flow rate is preferably entered into a microprocessor 62 from the detector 44. The microprocessor 62 in turn will control the speed of fan motor 64 and thus the air displacement of fan 65. The blower speed can be adjusted to provide the required residence time.

Figure 2:
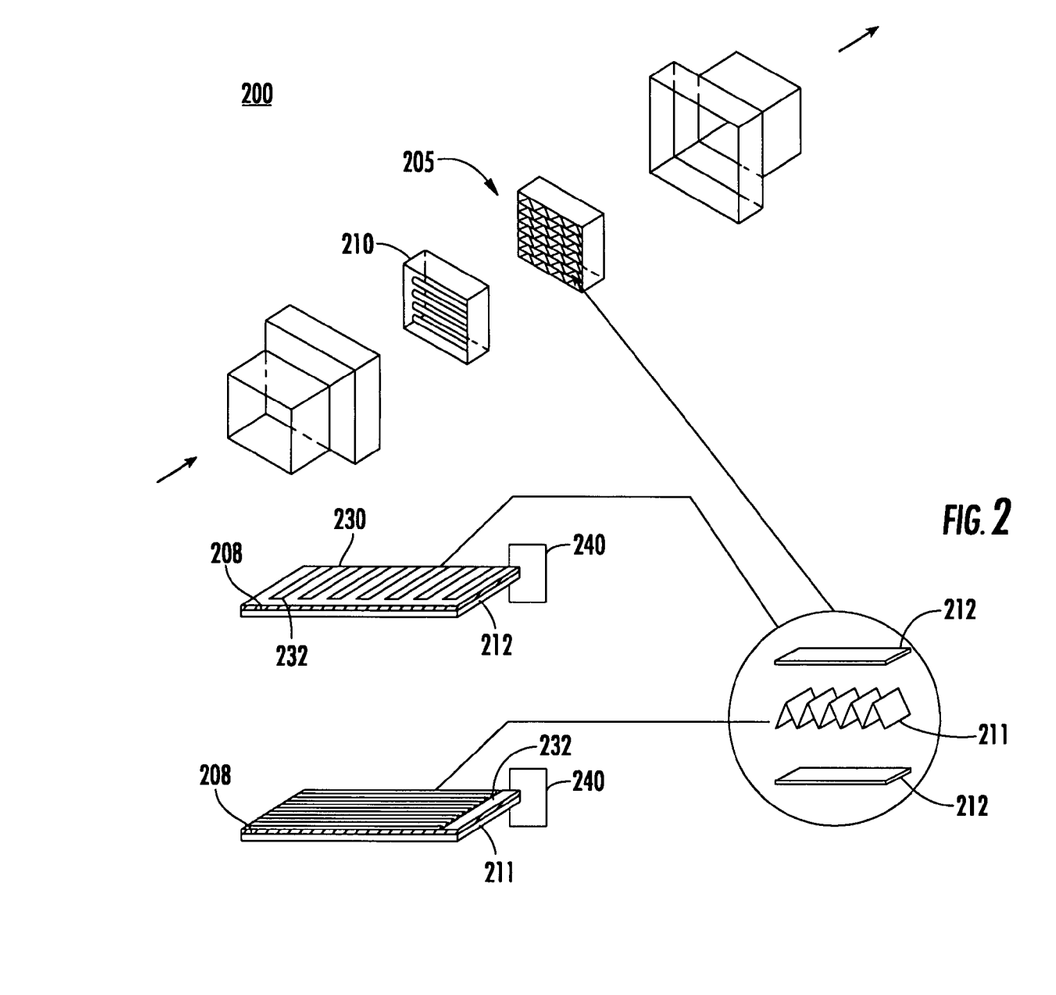
FIG. 2 is an exploded diagrammatic view illustrating components of a first embodiment of the reactor unit which includes an electrical connection between a metal grid which is electrically coupled to the front portion of photocatalyst particles and the back of the photocatalyst particles, according to an embodiment of the invention.

FIG. 2 diagrammatically illustrates components of a first exemplary reactor unit 200 which can be used as reactors 21 and 22 shown in FIG. 1. These components include a catalytic filter 205 and a bank of lamps 210. At least a portion of the photons emitted by lamps 210 have an energy at least equal to the band gap energy of the photcatalyst. In typical applications, lamps 210 preferably deliver low energy photons of the UV-A and lower energy portion of the UV-B spectrum. A UV wavelength between about 300 and about 400 nm is generally preferred. For example, low pressure mercury lamps (Southern New England RPR-3500A) with an input energy of 14 W can be used. Each lamp emits approximately 1.5 W of UV-radiation, predominately at about 350 nm.

Light from UV lamps 210 is directed towards catalytic filter 205. Catalytic filter 205 includes alternating photocatalyst coated corrugated substrate elements 211 and photocatalyst coated planar substrate elements 212. A photocatalyst layer 208 comprising a plurality of photocatalyst particles, such as $TiO_2$ particles, are secured to at least one side of substrate elements 211 and 212. Although photocatalyst layers 208 are shown disposed on only one side of filter substrate elements 211 and 212, photocatalyst layers may be disposed on both sides of corrugated substrate elements 211 and 212. Gaps (not shown) are provided between photocatalyst layers 208 in photocatalytic filter 205 to provide sufficient air space to permit air passage therethrough with a minimum of pressure drop.

In one embodiment, substrates 211 and 212 can be a fibrous media, such as a fibrous woven or non-woven material, analogous to common air conditioning filters. Substrate 211 and 212 can be HEPA or HEPA-like. At least some of the fibers are preferably electrically conducting fibers, such as metal fibers, electrically conducting polymer fibers, electrically conducting carbon fibers or carbon nanotubes. Some examples of non-electrically conducting fibers and materials for the substrate 211 and 212 which are preferably mixed with electrically conducting fibers include natural fibers such as cotton and wool, man-made and synthetic fibers such as rayon, polyester, polypropylene and polytetrafluoroethylene, and other materials such as flame resistant fibrous materials and carbons and all other functional fibrous materials.

Catalytic filter 205 includes structure for significantly reducing hole-electron recombination in the form of an electrically conductive shunting structure to remove photogenerated electrons before they can recombine with photogenerated holes. Each photocatalyst layer 208 can be provided its own shunting structure. FIG. 2 shows electrically conductive (e.g. metallic) grids 230 disposed on photocatalyst layers 208, grids 230 comprising a plurality of spaced apart electrically conductive strips 232. Spacing between conductive strips 232 is provided to allow UV light to reach the photocatalyst particles comprising photocatalyst layer 208.

However, if optically transparent electrically conductive materials are used, grid 230 can be replaced by a continuous sheet (not shown). For example, fluorine doped $SnO_2$ is known to be substantially optically transparent in the UV range from the violet edge of the visible spectrum (about 400 nm) to about 260 nm.

The strips 232 comprising grid 230 are preferably thin and narrow metallic strips. Grid 230 is connected to an electrically conductive pathway to facilitate removal of electrons generated by the photocatalyst particles comprising photocatalyst layer 208 by allowing photogenerated electrons which reach grid 230 to be shunted away. Shunt wire 240 electrically connects grid 230 to the back of substrates 211 and 212. A single shunt wire 240 can make electrical connection to the plurality of substrates 211 and 212, or each substrate 211 and 212 can be provided a separate shunt wire 240.

Optionally, in applications such as industrial applications where the electron flow generated is comparatively large, one or more low value resistors (not shown) can be placed in the pathway of shuntwire 240 to permit utilization of the electron flow in shunt wire 240. For example, a resistor having a value of several hundred milliohms to several ohms can be used.

If filter substrates 211 and 212 are not electrically conductive, the substrates 211 and 212 can be coated with an electrically conductive layer (not shown), such as aluminum. In this embodiment, shunt wire 240 would connect grid 230 to the electrically conductive coating layer. Alternate shunting arrangements will be apparent to those having ordinary skill in the art. For example, metallic grid 230 can be connected to a common external ground via a wire connector (not shown). Thus, in any of the above described embodiments, reactor unit 200 directs a substantial portion of the photogenerated electrons by photocatalyst layer 208 away from photocatalytically generated holes avoiding electron-hole recombination reactions, thus increasing the quantum efficiency of reactor unit 200.

Essentially any material capable of catalyzing photocatalytic oxidation when illuminated with a source of photons in the presence of air having a relative humidity greater than about 15 to 20% is suitable for use as a photocatalyst in the present invention. Such materials are readily identified by those of ordinary skill in the art without undue experimentation. Examples of suitable photocatalysts are semiconductor materials such as $ZnO_2$, $TiO_2$, and the like.

A thick slurry of TiO$_2$ (or other photocatalyst) can be made by mixing TiO$_2$ (or other photocatalyst) powder and deionized water. The TiO$_2$ solution is then mixed well by placing a flask with the thick TiO$_2$ slurry on a magnetic stirrer. Using a foam brush, the TiO$_2$ can be coated on one or both sides of solid surfaces 225. The solid surfaces 225 should be dried, such as for six hours, then another coat of TiO$_2$ can be applied. A heat gun can be used to accelerate the drying of the surfaces. After the solid surfaces are dry and the TiO$_2$ is sufficiently affixed, the catalytic filter 205 is ready for use, such as in a recirculating duct. However, heat treatment of the coated substrate at an appropriate temperature may be necessary to secure the coating to the substrate.

The present invention also contemplates providing a photocatalyst-coated surface in a duct section by painting the interior duct walls with the photocatalyst coating and laying a metallic grid 230 or equivalent structure thereon. UV lamps are then installed in the duct to illuminate the photocatalyst-coated interior duct walls.

The current flowing along the metallic grid 230 can be utilized for a variety of useful purposes. For example, electrons collected can be used in reduction reactions, such as to remove metal oxides from water. Electrons collected can also be used to generate light or collected in a suitable energy storage unit for later use.

The metallic grid 230 preferably includes materials that are toxic to micro-organisms, such as the element silver. Silver can be provided in electrically conducting compound alloys, and include Ag containing compounds such as silver nitrate. Other materials toxic to the microorganisms of interest can also generally be used with the invention. Thus, microorganisms entering reactor unit 200 will die on contact with metallic grid 230 and will then be oxidized by enhanced photocatalysis provided by reactor 200. Metal ions may also be dispersed in the catalyst layer 208 to accelerate the kill rate of micro-organisms and increase the rate of photocatalysis further.

The metallic grid 230 may be formed by a variety of known methods. For example, screen printing or vapor deposition can be used. In addition, metal grid 230 may be formed from precipitation of metal from suitable metal compounds by action of light or some other reaction.

Figure 3:
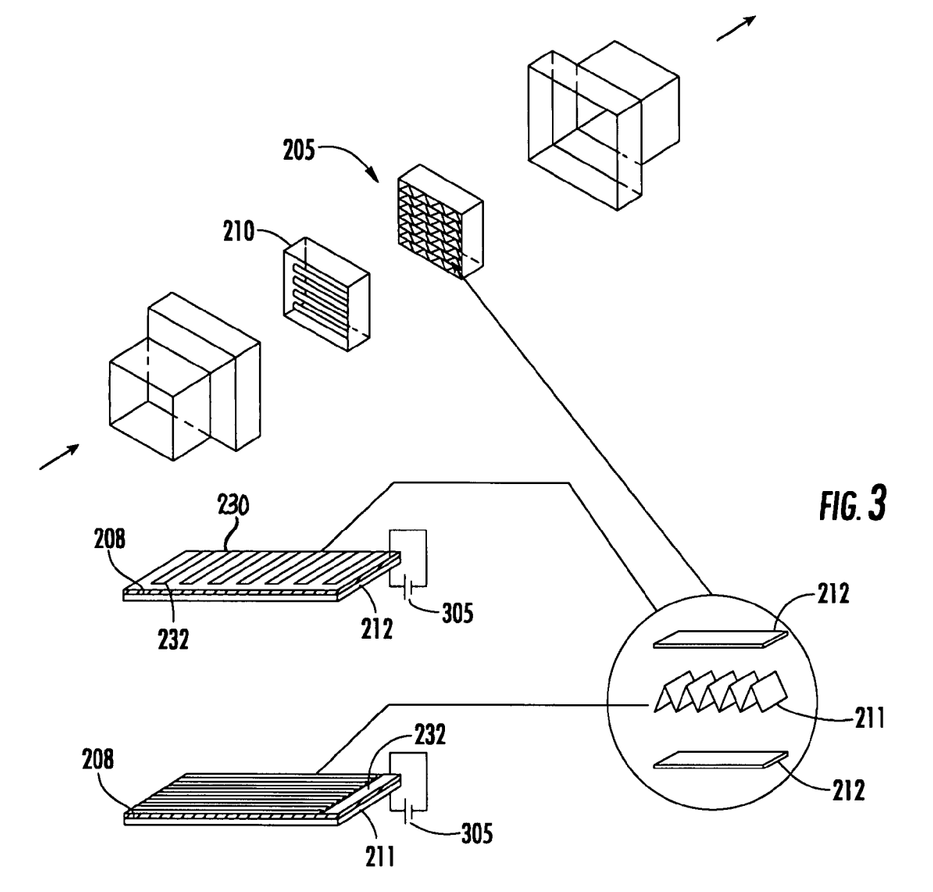
FIG. 3 is an exploded diagrammatic view illustrating components of a second embodiment of the reactor unit which includes an electrical connection and an applied DC bias between the front and back portions of photocatalyst particles, according to an embodiment of the invention.

FIG. 3 shows a reactor 300 according to an alternate embodiment of the invention. Reactor 300 include a power supply 305 for providing a DC bias across photocatalyst layers 208. This arrangement can further improve the efficiency of the disinfection process by driving photogenerated holes and electrons in different directions. Although generally not preferred, an AC bias may also be used.

The applied bias is preferably sufficient to keep the electrons separated from the holes in the photocatalyst by directing them in different directions. It may also be possible for the anode bias to be sufficient in the absence of a photochemical reaction to cause electrochemical oxidations. However, since the photocatalyst material is a semiconductor with high energy band gap, such as 3.2 eV for TiO$_2$, a very large bias would generally be needed to provide sites for electrochemical oxidation in the absence of light of appropriate wavelength. Magnetic separation of electrons and holes through providing a magnetic field may also be used either alone or in conjunction with structures described above (not shown).

Figure 4:
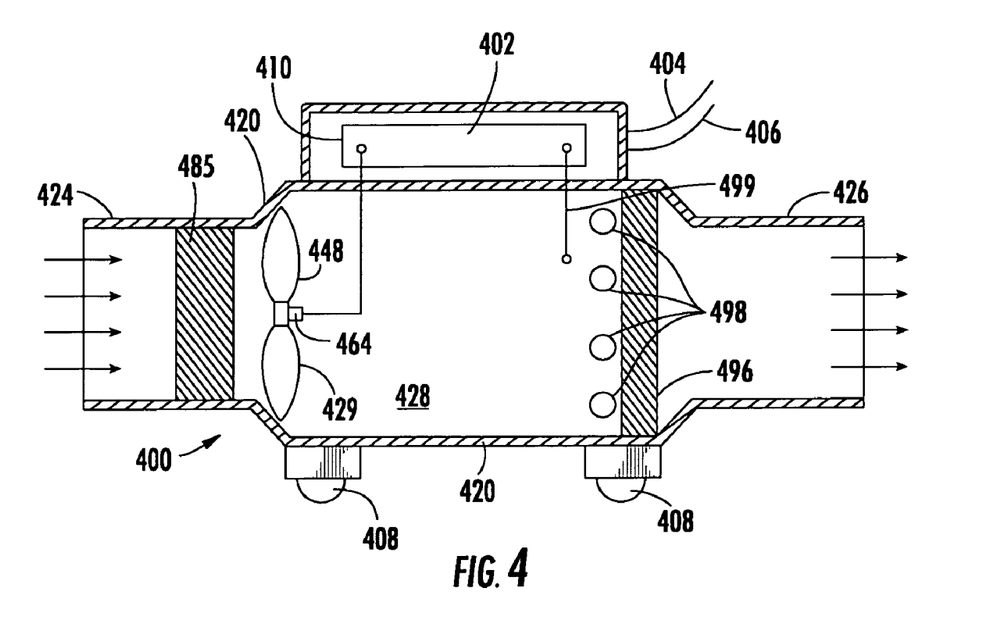
FIG. 4 is a longitudinal cross-sectional view of a stand-alone embodiment of the invention.

The essentials of the invention can be utilized independent of a duct system. Such a stand-alone unit 400 is shown in FIG. 4. The unit 400 includes a housing 420 having an inlet 424 and an outlet 426. Intermediate the inlet and outlet is a chamber 428 that includes a control fan 429, a fan motor 464 for driving fan 448, and catalytic filter 496 upon which UV light is directed from a series of UV lamps 498. An air speed detector 499 determines the air flow displacement. A second chamber 410 is provided on the housing 420 to enclose a microprocessor 402. The electric power for the unit 400 is provided to the system through the control processor 402 via leads 404 and 406. The stand-alone unit 400 may be operated without the airspeed detector 499, if the unit 400 is designed and constructed with a constant air flow rate fan 448 matched with the cross sectional area of the housing 420 to provide the desired residence time for the air flow over the catalyst.

A particulate prefilter 485 is provided to maintain the interior of the stand-alone unit free of dirt that might damage catalytic filter 496. Catalytic filter can be a filter based on the inventive arrangement shown in FIG. 2 or FIG. 3. The particulate prefilter can be any commercially available unit, or a commercially available unit coated with photocatalyst particles.

The stand-alone unit 400 can be supported by wheels 408 so that it can be easily moved to a position within the room where it is most likely to encourage air flow circulation throughout the entire room. Also, the stand-alone unit 400 can be utilized as an exhaust unit from a room in which undesirable fumes are present which one does not wish to exhaust into the atmosphere without treating them first. For instance, paint shops or in other industrial plants, the stand-alone unit 400 can be built into a roof or any exterior wall or it can be adapted for window support in the same fashion as a room air conditioner. In any event, contaminated air is cleansed before reaching the atmosphere.

The invention can be used to improve existing filter types. For example, the invention can be used together with electrostatic filters or photocatalytic electrostatic filters. Such combinations can be integrated into a single filter, or used together in a serial arrangement. Photocatalytic electrostatic filters are described in U.S. Pat. No. 5,993,738 to the same inventor as the current application and is hereby incorporated by reference in its entirety into the current application.

A method for disinfecting a fluid stream containing microorganisms or chemical contaminants includes the steps of providing a fluid stream and contacting the fluid stream with a plurality of photocatalyst surfaces which generate electrons and holes upon suitable irradiation. The photogenerated electrons and holes are directed away from one another to limit their recombination. At least a portion of the microorganisms or chemical contaminants are then photocatalytically oxidized at a rate enhanced by the reduced recombination rate provided by the invention.

The invention can be used in products for cleaning indoor air in buildings, and other enclosed spaces such as automobiles, airplanes and hospitals. The invention can also be useful against bioterrorism through application in mail rooms, train stations and airports.

The invention can be applied to envelopes and other surfaces, such as floors and walls, upon which, a layer of photocatalyst particles may be painted or otherwise applied and secured thereto. For example, applied to envelopes, an envelope can include a thin layer of photocatalyst particles, such as nanometers to tens of nanometers thick, on its surfaces. To provide disinfection, a metal grid can brought into contact with the photocatalyst layer provided by the envelope. The metal grid can be tied to an external ground, or between an external power supply and an external ground. Disinfection is then initiated by exposure of the coated envelope to light of the appropriate wavelength, wherein a substantial portion of the photogenerated electrons are directed away from photocatalytically generated holes thus reducing the rate of electron-hole recombination reactions and accordingly increasing the speed and efficacy of contaminant destruction. This method is preferably practiced using automated equipment that passes the articles through a light emitting arrangement, such as at a mail facility.

When products based on this process are used in building ventilation systems, they will help persons with asthma and allergy problems, and prevent the spread of disease through air. The invention can be used to help the military to combat chemical and biological warfare. The invention can also be used to trap spreading spores such as anthrax. In addition, the invention can be used to improve cleanliness in clean rooms which is known to help improve yields for products fabricated using high technology manufacturing processes, such as semiconductors.

Figure 5:
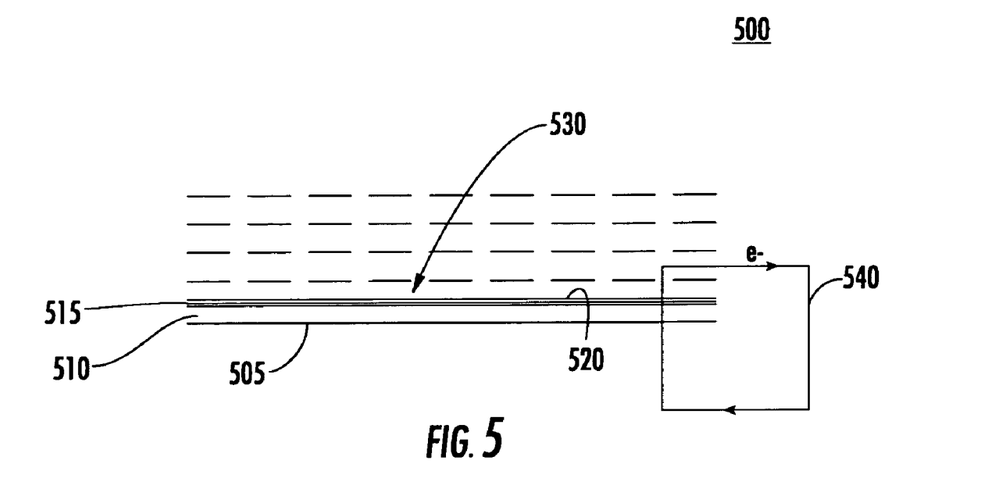
FIG. 5 illustrates a water purification system based on an embodiment of the invention.

The invention can also be used for liquid purification, such as water purification. FIG. 5 shows a water purification system 500 based on an embodiment of the invention. System 500 includes substrate layer 510 coated with a photocatalyst layer 515. A current collecting grid 520 is disposed on the photocatalyst layer 515. A metal back plate 505 is disposed on substrate 510 opposite photocatalyst layer 515. A connector 540 electrically couples grid 520 and metal back plate 505. Light 530 from a suitable light source incident on photocatalyst layer 515 generates hole-electron pairs. Electrons are collected by grid 520 and are shunted to metal back plate 505 via connector 540, thus increasing the rate of photoelectrochemical removal of contaminants in the water. Although not shown, a bias can be applied between grid 520 and metal back plate 505 to further increase the rate of photoelectrochemical removal of contaminants in the water.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

What is claimed is:

1. A system for disinfecting fluids, comprising:
    a photocatalyst layer comprising a plurality of photocatalyst particles for photogenerating electrons and holes, said photocatalyst layer having a top and a bottom surface, wherein said bottom surface is secured to a solid surface;
    a source of photons having a wavelength corresponding to at least a band gap energy of said photocatalyst, and;
    an electrically conductive layer disposed on and in electrical contact with said photocatalyst layer for removing a portion of said photogenerated electrons, said electrically conductive layer being interposed between said source of photons and said photocatalyst layer wherein incident light from said source of photons is transmitted by said electrically conductive layer to said top surface of said photocatalyst layer, said electrically conductive layer reducing an electron-hole recombination rate involving said photogenerated electrons and holes resulting in an increase in a removal rate of microorganisms or chemical contaminants from a fluid.

2. The system of claim 1, wherein said electrically conductive layer comprises a grid, said grid including a plurality of strips, spaces between said strips allowing said incident light to reach said photocatalyst layer.

3. The system of claim 1, wherein said photocatalyst layer includes a plurality of metal ions.

4. The system of claim 1, wherein said electrically conductive layer comprises a continuous sheet, said electrically conductive layer being substantially optically transparent for said wavelength of said photons to allow said incident light to be transmitted therethrough to reach said photocatalyst layer.

5. The system of claim 1, wherein said electrically conductive layer comprises a metal.

6. The system of claim 1, wherein said electrically conductive layer is connected to an external ground.

7. The system of claim 1, further comprising a source of electrical bias connected to said electrically conductive layer, said bias increasing said rate of removal of said photogenerated electrons.

8. The system of claim 1, wherein said electrically conductive layer comprises at least one material generally toxic to microorganisms.

9. The system of claim 8, wherein said electrically conductive layer comprises silver.

10. The system of claim 1, wherein said system is disposed in an air supply register of a heating, ventilating and air conditioning system or in an air duct.

11. A system for disinfecting air, comprising:
    a duct through which air is moved;
    a blower connected to said duct to move said air through said duct;
    a photocatalyst layer including a plurality of photocatalyst particles having a predetermined band gap energy for photogenerating electrons and holes, said photocatalyst layer having a top and a bottom surface, wherein said bottom surface is secured to a solid surface in said duct;
    a source of photons having a wavelength corresponding to at least a band gap energy of said photocatalyst;
    an electrically conductive layer disposed on and in electrical contact said photocatalyst layer, said electrically conductive layer being interposed between said source of photons and said photocatalyst layer, wherein incident light from said source of photons is transmitted by said electrically conductive layer to said top surface of said photocatalyst layer, said electrically conductive layer for directing said photogenerated electrons away from said photogenerated holes.

12. The system of claim 11, wherein said solid surface comprises at least one interior wall of said duct, said photocatalyst layer being coated onto said wall and said electrically conductive layer being coated on to said photocatalyst layer.

13. The system of claim 11, wherein said electrically conductive layer comprises a grid, said grid including a plurality of strips, spaces between said strips allowing said incident light to reach said photocatalyst layer.

14. The system of claim 11, wherein said photocatalyst layer includes a plurality of metal ions.

15. The system of claim 11, wherein said electrically conductive layer comprises silver.

16. The system of claim 11, wherein said electrically conductive layer comprises a continuous sheet, said electrically conductive layer being substantially optically transparent for said wavelength of said photons to allow said incident light to be transmitted therethrough to reach said photocatalyst layer.

* * * * *